United States Patent
Lim et al.

(10) Patent No.: US 9,377,410 B2
(45) Date of Patent: Jun. 28, 2016

(54) METHOD FOR MEASURING REACTION RATE OF REACTIVE MESOGEN

(71) Applicant: Samsung Display Co., Ltd., Yongin (KR)

(72) Inventors: Ho Lim, Suwon-si (KR); Tae-Min Kim, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 261 days.

(21) Appl. No.: 14/282,917

(22) Filed: May 20, 2014

(65) Prior Publication Data
US 2015/0185158 A1    Jul. 2, 2015

(30) Foreign Application Priority Data

Dec. 31, 2013 (KR) .................. 10-2013-0167940

(51) Int. Cl.
*G01N 21/77* (2006.01)
*G01N 21/64* (2006.01)
*G01N 21/75* (2006.01)

(52) U.S. Cl.
CPC .............. *G01N 21/77* (2013.01); *G01N 21/643* (2013.01); *G01N 2021/6439* (2013.01); *G01N 2021/755* (2013.01)

(58) Field of Classification Search
CPC ............................. G01N 21/77; G01N 21/643
USPC ................................................. 436/5, 34, 56
See application file for complete search history.

(56) References Cited

U.S. PATENT DOCUMENTS

| | | | | |
|---|---|---|---|---|
| 4,610,966 A * | 9/1986 | Fuchs | ............... | G01N 31/22 436/111 |
| 6,307,042 B1 * | 10/2001 | Goldberg | ............... | B01J 19/0046 506/16 |
| 6,607,918 B2 * | 8/2003 | LaGraff | ............... | G01N 33/20 436/166 |
| 8,304,242 B2 * | 11/2012 | Zhang | ............... | G01N 21/643 436/5 |
| 2001/0007733 A1 * | 7/2001 | Matsuyama | ........... | G02B 5/201 430/7 |

(Continued)

FOREIGN PATENT DOCUMENTS

| | | |
|---|---|---|
| CN | 103135286 | 6/2013 |
| EP | 2 597 134 | 5/2013 |

(Continued)

OTHER PUBLICATIONS

Contoret, A. E. A. et al, Chemistry of Materials 2002, 14, 1477-1487.*

(Continued)

*Primary Examiner* — Arlen Soderquist
(74) *Attorney, Agent, or Firm* — H.C. Park & Associates, PLC

(57) ABSTRACT

A method for measuring a reaction rate of a reactive mesogen and an alignment layer formed thereby, the method including coating an alignment material on a substrate. The alignment material includes a backbone and a reactive mesogen connected to the backbone. The reactive mesogen includes an unsaturated bond. The alignment material is irradiated with ultraviolet light, or is heated, to form the alignment layer. A marking compound, including a thiol group is coated on the alignment layer and reacts with remaining unreacted reactive mesogen, to form a marked mesogen. An amount of the marked mesogen is detected. A reactive ratio is measured by comparing an amount of the reactive mesogen before irradiating or heating with an amount of the marked mesogen.

19 Claims, 2 Drawing Sheets

(56) References Cited

U.S. PATENT DOCUMENTS

| | | | |
|---|---|---|---|
| 2004/0132092 A1* | 7/2004 | Stetson | G01N 33/583 435/7.1 |
| 2005/0130309 A1* | 6/2005 | Gjerde | G01N 31/16 436/34 |
| 2006/0257558 A1* | 11/2006 | Nomura | C08J 7/047 427/162 |
| 2010/0291685 A1* | 11/2010 | Zhang | G01N 21/643 436/5 |
| 2011/0143967 A1* | 6/2011 | McGall | C07F 7/188 506/32 |
| 2013/0129965 A1 | 5/2013 | Jeong et al. | |
| 2014/0063428 A1 | 3/2014 | Lee et al. | |
| 2015/0015840 A1* | 1/2015 | Imanishi | G02F 1/133723 349/123 |
| 2015/0079683 A1* | 3/2015 | Yager | G01N 21/77 436/5 |

FOREIGN PATENT DOCUMENTS

| | | |
|---|---|---|
| JP | 2012-256363 | 12/2012 |
| KR | 10-2008-0051796 | 6/2008 |
| KR | 10-2008-0057786 | 6/2008 |
| KR | 10-2012-0045680 | 5/2012 |
| KR | 10-2013-0057153 | 5/2013 |
| KR | 10-2014-0031668 | 3/2014 |

OTHER PUBLICATIONS

Yu, Y. et al, Chemistry of Materials 2004, 16, 1637-1643.* van Oosten, C. L. et al, Macromolecules 2008, 41, 8592-8596.*

Shimamura, A. et al, ACS Applied Materials & Interfaces 2011, 3, 4190-4196.*

* cited by examiner

METHOD FOR MEASURING REACTION RATE OF REACTIVE MESOGEN

CROSS REFERENCE TO RELATED APPLICATION

This application claims priority from and the benefit of Korean Patent Application No. 10-2013-0167940, filed on Dec. 31, 2013, which is hereby incorporated by reference for all purposes as if fully set forth herein.

BACKGROUND

1. Field

Exemplary embodiments of the inventive concept relate to a method for measuring a reaction rate of a reactive mesogen. More particularly, exemplary embodiments of the inventive concept relate to a method for measuring a reaction rate of a reactive mesogen according to an ultraviolet process or a thermal process, by including a marking compound capable detectable by spectroscopy.

2. Discussion of the Background

A liquid crystal display apparatus is one of the most widely used types of flat panel display FPD. Examples of a flat panel display include, but are not limited to, a liquid crystal display ("LCD"), a plasma display panel ("PDP") and an organic light emitting display ("OLED").

The liquid crystal display apparatus applies voltages to liquid crystal molecules to control the orientation thereof. As a result, optical characteristics of the liquid crystal cell, such as birefringence, optical activity, dichroism, and light scattering, may be controlled to display an image.

A liquid crystal display apparatus includes a liquid crystal display panel and a backlight assembly. Liquid crystal molecules of the liquid crystal display panel may be aligned in a specific direction to obtain a uniform brightness and a high contrast ratio.

Generally, a liquid crystal display apparatus includes a reactive mesogen in the liquid crystal to align the liquid crystal molecules. The reactive mesogen may be reacted via an ultraviolet process to pre-tilt of the liquid crystal.

Recently, an alignment layer including a reactive mesogen has been developed, to improve transmissivity and response time. The alignment layer may be formed from an alignment liquid that includes a compound including a polyimide molecule as a backbone and a reactive mesogen as a side chain.

Physical or chemical properties of the reactive mesogen and the backbone are similar with each other, so that it is difficult to measure a reaction rate of the reactive mesogen during the ultraviolet process. Thus, a smear on the liquid crystal display apparatus may be generated by a remaining reactive mesogen.

BRIEF SUMMARY OF THE INVENTIVE CONCEPT

Exemplary embodiments of the inventive concept provide a method for measuring a reaction rate of a reactive mesogen by using a marking compound.

According to an exemplary embodiment, a method for measuring a reaction rate of a reactive mesogen includes: coating an alignment material onto a substrate, the alignment material comprising alignment molecules that each comprise a backbone and a reactive mesogen connected to the backbone; reacting the reactive mesogens to form an alignment layer, by irradiating the alignment material with ultraviolet light or by heating the alignment material; forming a marked mesogen by coating a marking compound including a thiol group, on the alignment layer, to react unreacted reactive mesogen with the marking compound; detecting an amount of the marked mesogen; and measuring a reactive ratio by comparing an initial amount of the reactive mesogen with an amount of the marked mesogen.

It is to be understood that both the foregoing general description and the following detailed description are exemplary and explanatory and are intended to provide further explanation of the invention as claimed

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE INVENTIVE CONCEPT

Hereinafter, exemplary embodiments of the inventive concept will be explained in detail with reference to the accompanying drawings.

Figure 1:
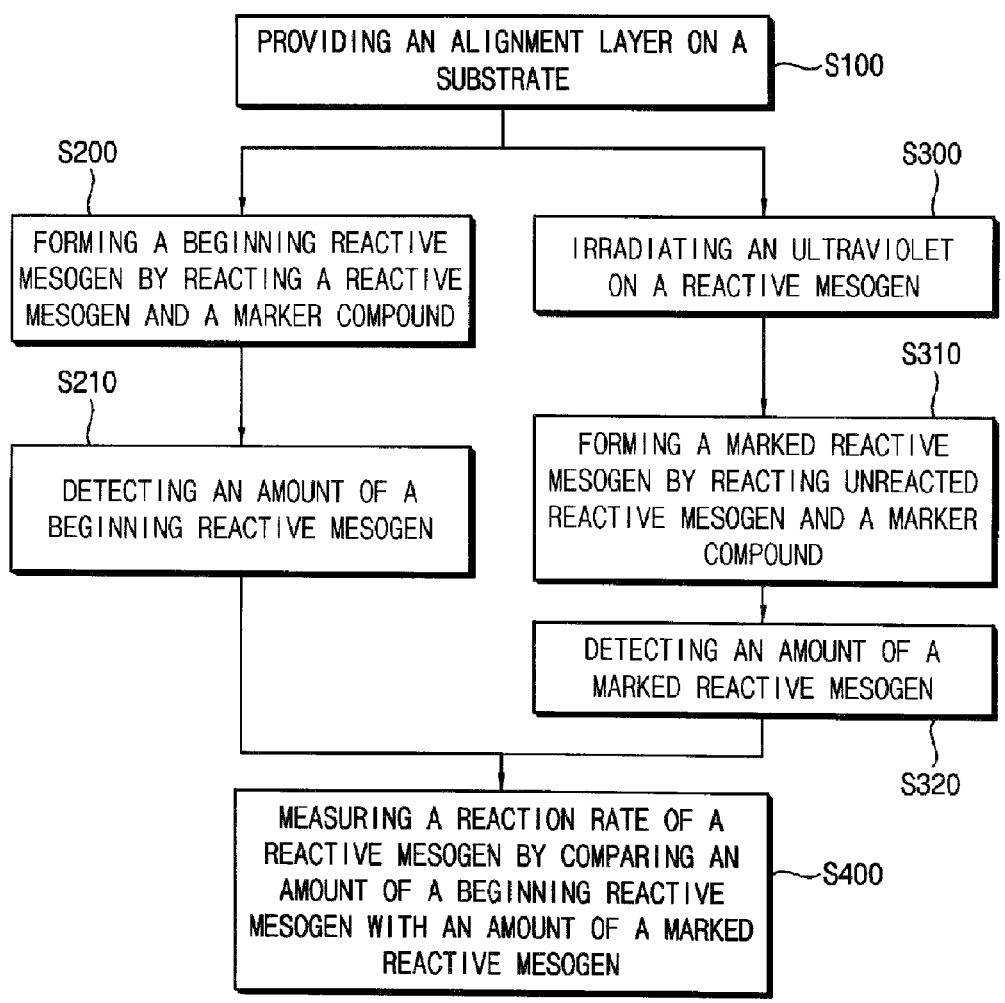
FIG. 1 is a diagram illustrating an exemplary embodiment of a method for measuring a reaction rate of a reactive mesogen
Figure 2:
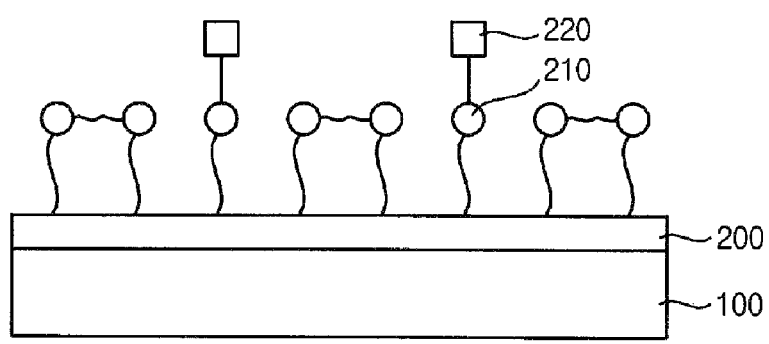
FIG. 2 is a cross-sectional view illustrating an exemplary embodiment of an alignment layer.

FIG. 1 is a diagram illustrating an exemplary embodiment of a method for measuring a reaction rate of a reactive mesogen. FIG. 2 is a cross-sectional view illustrating an exemplary embodiment of an alignment layer. Herein, a "reactive mesogen" refers to photo-curing particles, that is, a photo-crosslinkable low molecular weight copolymer or a photo-crosslinkable high molecular weight copolymer, and makes a chemical reaction such as a polymerization reaction when light having a certain wavelength, such as ultraviolet, is applied.

Referring to FIGS. 1 and 2, a method for measuring a reaction rate of a reactive mesogen includes: providing an alignment layer 200 on a substrate 100 (S100); forming a beginning reactive mesogen by reacting a reactive mesogen and a marker compound (S200); detecting an amount of a beginning reactive mesogen (initial amount of the reactive mesogen) (S210); irradiating an ultraviolet on a reactive mesogen (S300); forming a marked mesogen by reacting unreacted reactive mesogen and a marker compound (S310); detecting an amount of a marked mesogen (S320); and measuring a reaction rate of a reactive mesogen by comparing an amount of a beginning reactive mesogen with an amount of a marked mesogen (S400).

An alignment liquid may be coated on the substrate 100 to provide the alignment layer 200. For example, the alignment liquid may be coated by slit coating, spin coating, or the like.

The substrate 100 may include a first substrate and a second substrate. The first substrate and the second substrate may be a transparent insulation substrate. For example, the transparent insulation substrate may be a glass substrate, a plastic substrate, or the like.

A liquid crystal layer may be disposed between the first substrate and the second substrate. The liquid crystal layer may include liquid crystal molecules. When an electric field is not formed in the liquid crystal layer, a major axis of the liquid crystal molecules may be vertical (perpendicular) to the substrate 100.

A first electrode may be formed on the first substrate, and a second electrode may be formed on the second substrate. When a voltage is applied to the first electrode and the second electrode, the liquid crystal molecules in the liquid crystal layer may be aligned.

The alignment liquid may include compounds having a backbone and a side chain, and the side chain may include a reactive mesogen 210. The side chain may be combined with the backbone. The alignment liquid may include unsaturated bond on a terminal of the side chain. For example, the backbone may be polyethylene, polyimide, polyphosphazene or the like.

The reactive mesogen 210 may include a reactive mesogen unit and a photoreactive group.

For example, the reactive mesogen unit may include

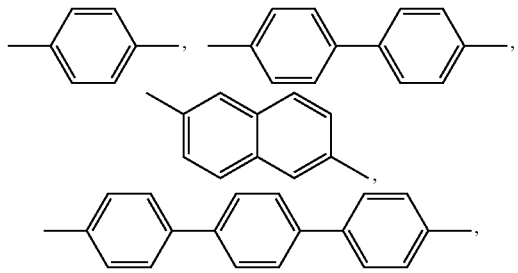

or the like.

The reactive mesogen 210 may include the photoreactive group for a photoreaction. The photoreactive groups adjacent to each other may form a cross-linkage by irradiation with ultraviolet light.

The photoreactive group may include an unsaturated bond. For example, the photoreactive group may include

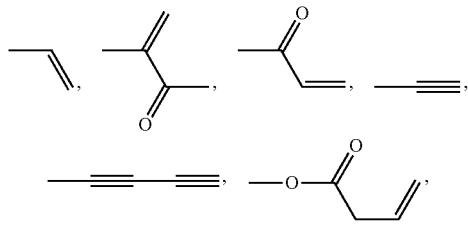

or the like.

The alignment liquid may be coated on the substrate 100 to provide the alignment layer 200. A voltage may be applied to the first electrode and the second electrode, thereby forming an electric field in the liquid crystal layer. The liquid crystal molecules may have a pre-tilt angle with respect to the substrate 100 in accordance with the electric field. The voltage may be within a range of about 10V to about 30V.

The ultraviolet light may irradiate the alignment layer 200, thereby reacting the reactive mesogen 210. An exposure intensity of the ultraviolet light may be equal to or greater than 10 J/cm$^2$.

The photoreactive groups of the reactive mesogen 210 may react with each other when irradiated by ultraviolet light, thereby forming bonds. A reaction rate between the photoreactive groups may vary according to the exposure intensity of the ultraviolet light.

After the reactive mesogen 210 is irradiated, a marking compound 220 may be coated on the alignment layer 200. For example, the marking compound 220 may be coated by slit coating, spin coating, or the like.

The marking compound 220 may include a thiol group (SH). The marking compound 220 may be represented by the following Chemical Formula 1.

<Chemical Formula 1>

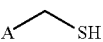

For example, A may be

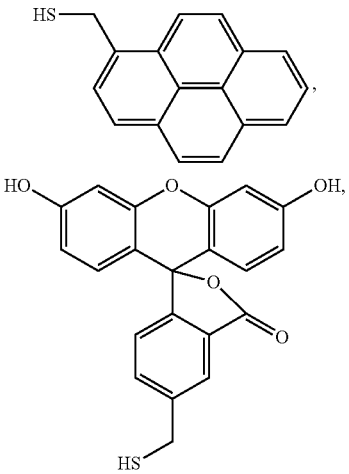

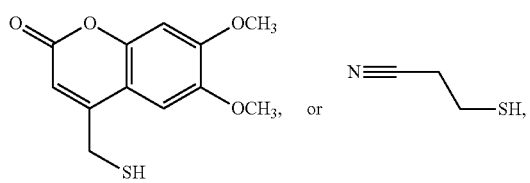 [SMILES: COc1cc2oc(=O)cc(CS)c2cc1OC ; N#CCCS]

$HS-(CH_2)_n-CF_3$, $HS-(CF_2)_n-CF_3$.

The marking compound 220 may be formed by reacting an alkyl halide with thiourea, according to the following Reaction Formula 1.

<Reaction Formula 1>

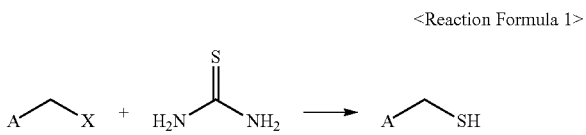

The thiol group of the marking compound 220 may react with the unsaturated bond of the reactive mesogen 210. The thiol group may react with the unsaturated bond by an thiol-ene reaction or a thiol-yne reaction.

For example, when the terminal of the reactive mesogen 210 includes a double bond, the reactive mesogen 210 may react with the marking compound 220 by the thiol-ene reaction represented by the following Reaction Formula 2.

<Reaction Formula 2>

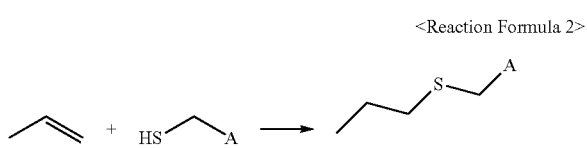

Therefore, a remaining reactive mesogen 210, which is not reacted, may react with the marking compound 220, thereby forming a marked mesogen. An amount of the marked mesogen may be measured by various spectroscopic methods. The spectroscopic methods may be applied according to the marking compound marking the marked mesogen.

For example, the marked mesogen may be detected by a UV-Vis spectrophotometer, a photoluminescence spectrometer, an FT-IR spectrometer, or an X-ray photoelectron spectrometer. For example, the marked mesogen may be detected by a UV-Vis spectrophotometer.

The marking compound may include a functional group, such as a benzene ring, which is capable of being detected by a UV-Vis spectrophotometer. Thus, an intensity of fluorescence of the marked mesogen is greater than an intensity of fluorescence of the reactive mesogen.

For example, the marking compound may include

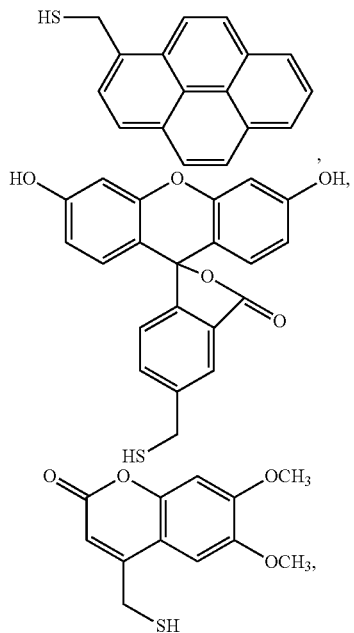

or a mixture thereof. An absorbance of the marked mesogen may be greater than an absorbance of the reactive mesogen, at a wavelength of at least 370 nm. An intensity of fluorescence of the marked mesogen may be greater than an intensity of fluorescence of the reactive mesogen, at a wavelength of at least 410 nm.

An amount of the marked mesogen may be measured by comparing the absorbance or the intensity of the fluorescence. For example, the marked mesogen may be detected by an FT-IR spectrometer.

The marking compound may include a functional group, such as a cyano group, which is capable of being detected by an FT-IR spectrometer. An absorption wavelength of the reactive mesogen and an absorption wavelength of the marked mesogen may be different from each other. Thus, the absorption wavelength of the marked mesogen may further include a specific absorption wavelength different from the absorption wavelength of the reactive mesogen.

For example, the marking compound may include

A maximum absorption wavelength of the marked mesogen may range from about 2,200 $cm^{-1}$ to about 2,300 $cm^{-1}$.

An amount of the marked mesogen may be measured by comparing the absorption wavelength and the strength of the absorption wavelength. For example, the marked mesogen may be detected by an X-ray photoelectron spectrometer ("XPS"). The marking compound may include a functional group, such as fluorine atom, which is capable of being detected by XPS.

A wavelength of a bonding energy of the reactive mesogen and a wavelength of a bonding energy of the marked mesogen may be different from each other. Thus, a specific wavelength of the bonding energy of the marked mesogen may be different from a specific wavelength of the bonding energy of the reactive mesogen.

For example, the marking compound may include HS—$(CH_2)_n$—$CF_3$, HS—$(CF_2)_n$—$CF_3$, or a mixture thereof. Thus, the wavelength of the bonding energy of the marked mesogen may further include a specific wavelength of the bonding energy in a range of about 690 eV to about 700 eV.

Thus, an amount of the reactive mesogen, which is not reacted by ultraviolet exposure, may be measured by various spectroscopic methods. Furthermore, an amount of the reactive mesogen, which is not exposed by ultraviolet, may be measured and compared with that of the marked mesogen. Therefore, the reaction rate of the reactive mesogen may be measured.

The alignment liquid may be coated on the substrate 100 to provide the alignment layer 200. For example, the alignment liquid may be coated by slit coating, spin coating, or the like.

The marking compound may be coated on the alignment layer 200. For example, the marking compound may be coated by slit coating, spin coating, or the like. The marking compound 220 may include a thiol group (SH). The marking compound 220 may be represented by the Chemical Formula 1.

The thiol group of the marking compound 220 may react with the unsaturated bonds of the reactive mesogen 210. The thiol groups may react with the unsaturated bonds by a thiol-ene reaction or a thiol-yne reaction.

The reactive mesogen may react with the marking compound to form a beginning reactive mesogen. The beginning reactive mesogen may be detected by various spectroscopic methods, so that an amount of the reactive mesogen prior to ultraviolet exposure, may be measured.

The reaction rate of the reactive mesogen may be measured by comparing an amount of the beginning reactive mesogen with an amount of a marked mesogen. Thus, an intensity of ultraviolet light exposure may be determined by using the method for measuring the reaction rate of the reactive mesogen.

The alignment liquid may be coated on the substrate 100, and then the coated alignment liquid may be exposed to ultraviolet light, to react the reactive mesogen and form the alignment layer 200. The intensity of ultraviolet light exposure may be controlled, so that the reaction rate of the reactive mesogen may be controlled.

The reactive mesogen may be reacted by exposing the alignment liquid with a first intensity of the ultraviolet light. For example, the first intensity may be at least 10 J/cm².

The reaction rate may be measured by comparing an amount of the beginning reactive mesogen and an amount of the marked mesogen after exposure at the first intensity. Furthermore, a second alignment layer may be formed by reacting the reactive mesogen with a second intensity of the ultraviolet light, after applying the alignment material to a second substrate. For example, the second intensity may be greater than the first intensity. The reaction rate at the second intensity can then be measured after marking with the marking compound to form a second marked mesogen.

The reaction rate at the second intensity may be measured by comparing an initial amount of the reactive mesogen and an amount of the second marked mesogen. An intensity of ultraviolet may be determined by comparing the reaction rate of the reactive mesogen exposed at the first intensity and the reaction rate of the reactive mesogen exposed at the second intensity. Thus, a process time and a process cost may be reduced.

Furthermore, an amount of a remaining reactive mesogen, which does not react, may be minimized, so that a thermal reaction of the remaining reactive mesogen during a high temperature process may be minimized. Thus, smears on a screen may be prevented, and a display quality may increase.

According to an exemplary embodiment, a method for measuring a reaction rate of a reactive mesogen may be used in a method for manufacturing a liquid crystal display apparatus, an organic light emitting apparatus, or the like.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method for measuring a reaction rate of a reactive mesogen comprising:
   applying an alignment material to a substrate, the alignment material comprising alignment molecules that each comprise a backbone and a reactive mesogen connected to the backbone;
   reacting the reactive mesogen to form an alignment layer, by irradiating the alignment material with ultraviolet light having a first intensity, or by heating the alignment material;
   applying a marking compound comprising a thiol group to the alignment layer, the marking compound configured to react with any remaining unreacted reactive mesogen, thereby forming a marked mesogen;
   detecting an amount of the marked mesogen; and
   measuring a first reactive ratio by comparing an initial amount of the reactive mesogen with the detected amount of the marked mesogen.

2. The method of claim 1, wherein the reactive mesogen comprises a photoreactive group comprising an unsaturated bond.

3. The method of claim 2, wherein the photoreactive group comprises at least one selected from the group consisting of

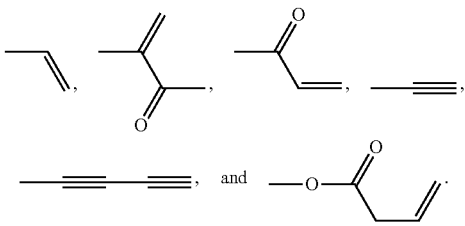

4. The method of claim 1, wherein the thiol group of the marking compound reacts with the unsaturated bond of the reactive mesogen.

5. The method of claim 1, wherein the marking compound is formed by reacting an alkyl halide with thiourea.

6. The method of claim 1, wherein the marked mesogen is detected using an ultraviolet-visible (UV-Vis) spectrophotometer or a photoluminescence spectroscopy device.

7. The method of claim 6, wherein the marked mesogen has a higher fluorescence intensity than the reactive mesogen.

8. The method of claim 7, wherein the marking compound comprises at least one selected from the group consisting of

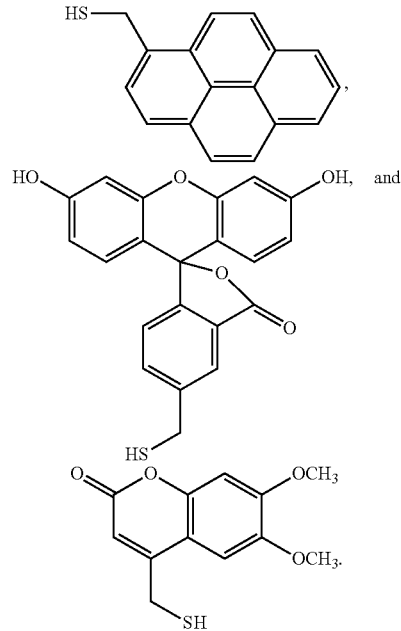

9. The method of claim 8, wherein an absorbance of the marked mesogen is greater than an absorbance of the reactive mesogen at a wavelength of at least 370 nm, or a fluorescence intensity of the marked mesogen is greater than a fluorescence intensity of the reactive mesogen, at a wavelength of at least 410 nm.

10. The method of claim 1, wherein the marked mesogen is detected using a Fourier transform infrared (FT-IR) spectrometer.

11. The method of claim 10, wherein an absorption wavelength of the marked mesogen and an absorption wavelength of the reactive mesogen are different from each other.

12. The method of claim 11, wherein the marking compound comprises

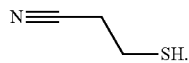

13. The method of claim 12, wherein a maximum absorption wavelength of the marked mesogen is in a range of about 2,200 cm$^{-1}$ to about 2,300 cm$^{-1}$.

14. The method of claim 1, wherein the marked mesogen is detected using an X-ray photoelectron spectrometer.

15. The method of claim 14, wherein a wavelength corresponding to a bonding energy of the marked mesogen and a wavelength corresponding to a bonding energy of the reactive mesogen are different from each other.

16. The method of claim 15, wherein the marked compound comprises at least one selected from the group consisting of HS—$(CH_2)_n$—$CF_3$ and HS—$(CF_2)_n$—$CF_3$.

17. The method of claim 16, wherein the wavelength of the bonding energy of the marked mesogen has a wavelength of a bonding energy in a range of about 690 eV to about 700 eV.

18. The method of claim 1, further comprising:
applying the alignment material to a second substrate;
irradiating the alignment material on the second substrate with ultraviolet light having a second intensity that is higher than the first intensity, to form a second alignment layer;
applying the marking compounds to the second alignment layer to form second marked mesogens;
detecting an amount of the second marked mesogens;
measuring a second reactive ratio by comparing an amount of the reactive mesogen before the second alignment layer is formed with the detected amount of the second reactive mesogens; and
comparing the reactive ratio and the second reactive ratio, to determine an ultraviolet intensity that results in the highest reactive ratio.

19. The method of claim 1, wherein the initial amount of the reactive mesogen is determined by:
applying an equal amount of the alignment material to a second substrate;
reacting the alignment material on the second substrate with the marking compound to form a beginning marked mesogen; and
detecting an amount of the beginning marked mesogen to determine the initial amount of the reactive mesogen.

\* \* \* \* \*